United States Patent [19]

Bugaut et al.

[11] 4,361,421
[45] Nov. 30, 1982

[54] HAIR-DYEING COMPOSITIONS BASED ON PARA-PHENYLENEDIAMINES

[75] Inventors: Andrée Bugaut, Boulogne-Billancourt; Ginette Jeanminet, Aulnay-sous-Bois, both of France

[73] Assignee: L'Oreal, Paris, France

[21] Appl. No.: 167,146

[22] Filed: Jul. 8, 1980

[30] Foreign Application Priority Data

Jul. 10, 1979 [FR] France ............................... 79 17888

[51] Int. Cl.³ .............................................. A61K 7/13
[52] U.S. Cl. .......................................... 8/407; 8/410; 8/412; 8/416
[58] Field of Search ..................... 8/412, 407, 410, 416

[56] References Cited

U.S. PATENT DOCUMENTS

| | | | |
|---|---|---|---|
| 3,884,627 | 8/1975 | Brody et al. | 8/410 |
| 4,268,264 | 5/1981 | Grollier et al. | 8/410 |
| 4,277,244 | 4/1981 | Bagaut et al. | 8/410 |

FOREIGN PATENT DOCUMENTS 2026553  2/1980  United Kingdom .................... 8/410

Primary Examiner—Donald B. Moyer
Attorney, Agent, or Firm—Fleit & Jacobson

[57] ABSTRACT

The invention relates to hair-dyeing compositions based on para-phenylenediamine. These compositions contain, as the oxidation dyestuff, para-phenylenediamine and one or more para-phenylenediamines of the formula

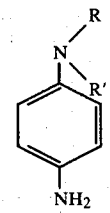

in which R denotes alkyl or hydroxyalkyl and R' denotes a hydroxyalkyl group, and also their cosmetically acceptable salts, in a molar ratio para-phenylenediamine/compound(s) of the formula (I), expressed in terms of free bases, which is such that, after the addition of an equal volume of hydrogen peroxide of 20 volumes strength and application to the hair for 30 minutes, no Bandrowsky's base is detected in the oxidizing dyeing composition.

These compositions make it possible to obtain natural background colorations, ranging from black to light chestnut, of very good quality.

9 Claims, No Drawings

HAIR-DYEING COMPOSITIONS BASED ON PARA-PHENYLENEDIAMINES

DESCRIPTION

The present invention relates to compositions intended to be used in the so-called oxidation dyeing of the hair, and to the dyeing processes using these compositions.

The use of para-phenylenediamine in hair dyeing, as a so-called oxidation dyestuff precursor of the paratype, is well known.

In an oxidising alkaline medium, and preferably in an ammoniacal medium in the presence of hydrogen peroxide, para-phenylenediamine by itself imparts so-called "background" colourations to the hair, which colourations can range from more or less light chestnuts to very dark browns shaded with red, depending on the concentrations used. In fact, after penetration into the hair fibre, para-phenylenediamine leads in situ, by means of an oxidative condensation process, to the formation of Bandrowsky's base, which is the coloured product responsible for these so-called background colourations. By associating, with para-phenylenediamine in the dyeing compositions for keratin fibres, various compounds commonly referred to as "meta compounds" or "couplers", it is possible to modify these background colourations in order to obtain a whole range of natural shades; black, more or less ashen, more or less warm and rich in very diverse sheens, such as blue, violet or copper.

For example, the addition of meta-phenylenediamines, and in particular 2,4-diaminoanisole, to para-phenylenediamine is commonly used in order to obtain blacks which are more or less shaded with blue.

The main couplers in current use are phenols, meta-aminophenols, meta-diamines or compounds with an active methylene group. By oxidative coupling with para-phenylenediamine, they lead to the formation of variously coloured indoanilines or indamines.

It is well known that the formation of these coloured compounds competes with the formation of Bandrowsky's base resulting from the oxidative condensation of para-phenylenediamine with itself, which condensation is much slower than that of para-phenylenediamine with the majority of couplers.

It is known, for example, that if para-phenylenediamine is associated either with resorcinol, or with 2,4-diaminoanisole or also meta-aminophenol, in equimolar amounts, the formation of Bandrowsky's base is virtually completely inhibited.

The complete harmlessness of Bandrowsky's base has been questioned in recent years and attempts have therefore been made to suppress its formation on the hair. Thus, in Belgian Pat. No. 597,393, it is specified that, in order to prevent the formation of Bandrowsky's base, which irritates the skin, products of the 1,4-diaminobenzene type are associated with equimolecular amounts of meta-diaminobenzene, meta-aminophenol or meta-diphenol. However, we have found that if the couplers are added in sufficient amounts to totally inhibit the formation of Bandrowsky's base, i.e. such that no base is detectable in the dyeing composition after application on the head for 30 minutes in the presence of hydrogen peroxide, the advantage of the background colouration provided by para-phenylenediamine itself is largely lost.

Furthermore, it should be noted that certain couplers, in particular the meta-phenylenediamines, such as 2,4-diaminotoluene, are not completely harmless. However, the meta-phenylenediamine couplers play a very important part in oxidation hair dyeing because they lead to the formation of blue indamines, blue being an essential fundamental colour for the production of blacks.

Furthermore, it has already been recommended, in oxidation hair dyeing, to use para-phenylenediamines of the general formula I:

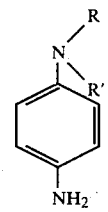

in which R denotes alkyl or hydroxyalkyl and R' denotes hydroxyalkyl, the alkyl groups having 2 to 4 carbon atoms, and also their salts and more particularly N,N-di-β-hydroxyethyl-para-phenylenediamine and N-ethyl-N-β-hydroxyethyl-para-phenylenediamine.

However, on oxidation with hydrogen peroxide, N,N-di-β-hydroxyethyl-para-phenylenediamine only imparts a grey-green colouration of low intensity to the hair, which is not of great value in hair dyeing. The association of this dyestuff precursor of the para-type with the metal compounds conventionally used thus makes it virtually impossible to formulate dyeing compositions which lead to medium chestnuts, browns and blacks. Likewise, on oxidation with hydrogen peroxide in an ammoniacal medium, N-ethyl-N-β-hydroxyethyl-para-phenylenediamine imparts a green colouration to the hair, which does not make it possible, when it is used as the only para compound in the dyeing compositions, to obtain a range of natural colourations other than the light shades.

We have now discovered, surprisingly, according to the present invention, that hair-dyeing compositions containing para-phenylenediamine in association with one or more oxidation bases of the formula (I), and preferably with N,N-di-β-hydroxyethyl-para-phenylenediamine or N-ethyl-N-β-hydroxyethyl-para-phenylenediamine or their cosmetically acceptable salts, cannot lead to the formation of Bandrowsky's base, in an amount detectable by chromatography, after the addition of an equal volume of hydrogen peroxide of 20 volumes strength and application on the head for 30 minutes, provided that this association corresponds to a well-selected molar ratio, regardless of the type of dyeing carrier used.

We have also discovered that, by using para-phenylenediamine with the compounds of the formula (I) in certain well-determined molar ratios such that the formation of Bandrowsky's base is avoided, it is possible to obtain, in hair dyeing, natural so-called "background" colourations, ranging from black to light chestnut, which are of very good quality, that is to say which are resistant to light, adverse weather conditions, washing and perspiration.

We have found, in particular, that the addition of compounds of the formula (I) to the dyeing compositions containing para-phenylenediamine, in the particular proportions required according to this invention, makes it possible to obtain noticeably darker shades than those obtained with the compositions containing an equal concentration of only para-phenylenediamine. Thus, the addition of N,N-di-β-hydroxyethyl-para-phenylenediamine to a composition containing 0.75% of para-phenylenediamine makes it possible to change from a medium chestnut to a very dark brown; the addition of N-ethyl-N-β-hydroxyethyl-para-phenylenediamine to a composition containing 0.35% of para-phenylenediamine makes it possible to change from a coppery blond to an ashen medium chestnut.

Furthermore, we have found that the association of para-phenylenediamine with the compounds of the formula (I), in the molar ratios required according to the invention, makes it possible to obtain shades which are less rich in red or purplish-red than the shades obtained with the compositions containing only para-phenylenediamine.

For example, the addition of N,N-di-β-hydroxyethyl-para-phenylenediamine to a dyeing composition containing 1.5% of para-phenylenediamine, in the proportions necessary according to the invention, makes it possible to change from a red-brown colouration to a raven black colouration.

This observation is essentially explained by the fact that the addition of an appropriate amount of a compound (or compounds) (I) to the dyeing compositions containing para-phenylenediamine inhibits the formation of Bandrowsky's base, the latter being replaced by new blue compounds resulting from an oxidative condensation between the two types of oxidation base present. It is these blue compounds which make it possible to obtain shades which are darker and less red, such as blue-blacks, blacks and ashen chestnuts.

The dyeing compositions of the present invention thus make it possible to obtain blue-blacks and blacks without the need to use couplers and, more particularly, without having to use meta-phenylenediamines which, by oxidative condensation with para-phenylenediamine, lead to blue indamines.

This fact constitutes a further advantage of the invention because it is known that certain meta-phenylenediamines are not completely harmless, and attempts have therefore been made to avoid their use in hair formulations. This is the case, in particular, of 2,4-diaminotoluene and 2,4-diaminoanisole.

In particular, we have found that, on 90% naturally white hair, a dyeing composition containing, for example, 1.5% of para-phenylenediamine and 3.5% of N-ethyl-N-β-hydroxyethyl-para-phenylenediamine dihydrochloride leads to a black colouration with a purplish-blue sheen, which is very close to the colouration imparted to hair from the same batch by a dyeing composition containing 1.5% of para-phenylenediamine, 0.15% of 2,4-diaminoanisole dihydrochloride and 0.5% of resorcinol, in the same dyeing carrier.

The present invention thus provides dyeing compositions containing para-phenylenediamine and one or more of the para-phenylenediamines of the formula (I) in certain well-defined molar ratios.

The present invention also provides a process for dyeing human hair using para-phenylenediamine and one or more of the para-phenylenediamines of the formula (I).

The hair-dyeing composition according to the present invention is essentially characterised in that it contains, as the oxidation dyestuff, in a preferably aqueous but cosmetically acceptable medium permitting the application of the dyestuffs to the hair, para-phenylenediamine, or a cosmetically acceptable salt thereof, and one or more para-phenylenediamines corresponding to the formula (I)

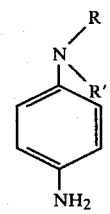

in which R denotes an alkyl or hydroxyalkyl group and R' denotes a hydroxyalkyl group, the alkyl groups having 2 to 4 carbon atoms, or a cosmetically acceptable salt of the latter, in a molar ratio para-phenylenediamine/para-phenylenediamine(s) of the formula (I), expressed in terms of free base, which is such that, after the addition of an equal volume of hydrogen peroxide of 20 volumes strength and application of the hair for 30 minutes, no Bandrowsky's base is detected in the oxidising dyeing composition.

It is considered, according to the invention, that no Bandrowsky's base in the oxidising dyeing composition can be detected when it is not detected by chromatography on a Schleicher and Schüll F 1500 LS 254 plate, regardless of the type of dyeing carrier used. For this purpose, a spot of a solution of orthoaminophenol is applied to the plate beforehand, at the point where the oxidising dyeing solution is subsequently to be applied. It is thus possible to have an exact picture of the amount of Bandrowsky's base which has actually been formed during the application to the hair. This is because the ortho-aminophenol prevents the formation of Bandrowsky's base on the silica plate, by the oxidative self condensation of any para-phenylenediamine which is still present at the end of the application. The condensation of para-phenylenediamine with ortho-aminophenol is in fact an extremely rapid reaction and much more rapid than the rate of formation of Bandrowsky's base so that any para-phenylenediamine reacts with the ortho-aminophenol rather than with itself.

The para-phenylenediamines of the formula (I) which are more particularly preferred according to the invention are N,N-di-β-hydroxyethyl-para-phenylenediamine and N-ethyl-N-β-hydroxyethyl-para-phenylenediamine.

The cosmetically acceptable salts are preferably hydrochlorides, hydrobromides or sulphates.

The dyeing compositions according to the present invention can essentially be classed in two categories according to whether they make it possible to obtain blacks or extremely dark browns, or whether they make it possible to obtain shades ranging from light chestnuts to very deep chestnuts.

The invention thus also provides, on the one hand, dyeing compositions for human hair which make it possible to obtain black or dark brown shades and which are characterised in that they contain from 1.5 to 2.5% by weight of para-phenylenediamine and in that the molar ratio para-phenylenediamine/compound(s) of the formula (I) (expressed as free base) is equal to about 0.5, and, on the other hand, dyeing compositions for human hair which lead to shades ranging from light chestnuts to very deep chestnuts and which are characterised in that they contain from 0.2 to 1.5% of para-phenylenediamine and in that the molar ratio para-phenylenediamine/compound(s) of the formula (I) is equal to or less than 1 but not less than 0.5.

The concentration of para-phenylenediamine in the compositions according to the invention is preferably 0.2 to 2.5% by weight, expressed in terms of free base, in particular 0.3 to 1.5% by weight.

In order to shade and enrich, with a sheen, the colourations obtained using the composition according to the invention, for example by adding warm golden or coppery sheens to chestnuts and browns, it is possible to add, to the compositions according to the invention, direct dyestuffs, such as azo and anthraquinone dyestuffs, and preferably nitro benzene derivatives, such as 2-N-($\beta$-hydroxyethyl)-amino-5-nitroanisole, 3-nitro-4-aminophenol, 3-nitro-4-N-($\beta$-hydroxyethyl)-aminophenol, ortho-nitroaniline, 3-nitro-4-N-methylamino-N,N-di-($\beta$-hydroxyethyl)-aniline, 2-amino-3-nitro-phenol, 2-amino-3-nitro-isopropyl-benzene, 2-methyl-4-amino-5-nitrophenol, 3-nitro-4-N'-($\beta$-hydroxyethyl)-amino-N,N-di-($\beta$-hydroxyethyl)-aniline and 2-N-($\beta$-hydroxyethyl)-amino-5-nitrophenoxy-ethanol.

The colouring agents other than the para-phenylenediamines are preferably present in an amount from 0.02 to 3% by weight, and especially 0.1 to 2% by weight, based on the total weight of the composition.

The pH of the dyeing compositions according to the invention is suitably 8 to 11.5 and preferably 9 to 11. The pH of these compositions can be adjusted to the desired value by means of an alkalising agent, such as ammonia, alkali metal carbonates, alkanolamines, such as mono-, di- or tri-ethanolamine, or alkylamines.

The dyeing compositions according to the invention can also contain anionic, cationic, non-ionic and/or amphoteric water-soluble surface-active agents. Amongst the surface-active agents which are more particularly preferred, there may be mentioned soaps, alkylbenzenesulphonates, alkylnaphthalenesulphonates, sulphates, ether-sulphates and sulphonates of fatty alcohols, quaternary ammonium salts, such as trimethyl-cetylammonium bromide and cetylpyridinium bromide, diethanolamides of fatty acids, polyoxyethyleneated or polyglycerolated acids and alcohols, polyoxyethyleneated or polyglycerolated alkylphenols and also polyoxyethyleneated alkylsulphates. The surface-active agents are suitably present in the compositions according to the invention in amounts from 0.5 to 55% by weight, and preferably 4 to 40% by weight, relative to the total weight of the composition.

The compositions can also contain organic solvents for solubilising compounds which would otherwise not be sufficiently soluble in water. Typical such solvents include lower alkanols, such as ethanol and isopropanol, glycerol, glycols or glycol ethers, such as ethylene glycol monobutyl ether (butylglycol), ethylene glycol, propylene glycol, diethylene glycol monoethyl ether and monomethyl ether, and analogous products and mixtures thereof. These solvents are preferably present in proportions from 1 to 40% by weight, and more particularly from 3 to 30% by weight, relative to the total weight of the composition.

The compositions according to the invention can be thickened, preferably with compounds such as sodium alginate, gum arabic, cellulose derivatives, such as methylcellulose, hydroxyethylcellulose, hydroxypropylmethylcellulose and carboxymethylcellulose, and various polymers performing this function, in particular acrylic acid derivatives. It is also possible to use inorganic thickeners, such as bentonite. These thickeners are preferably present in proportions of 0.5 to 5% by weight, and in particular 0.5 to 3% by weight, relative to the total weight of the composition.

Antioxidants, such as sodium sulphite, thioglycolic acid, sodium bisulphite, ascorbic acid and hydroquinone, can also be added to the compositions according to the invention. These antioxidants are advantageously present in the composition in proportions of 0.05 to 1.5% by weight, relative to the total weight of the composition.

It is of course possible to add, to the compositions according to the invention, any other adjuvants normally used in hair-dyeing compositions, in particular penetrating agents, sequestering agents, buffers, film-forming agents and perfumes.

The dyeing compositions according to the invention can be presented in various forms, such as a liquid, cream or gel, or in any other form suitable for dyeing the hair. In particular, they can be packaged in aerosol flasks in the presence of a propellant.

The dyeing processes using the dyeing compositions according to the invention consist in mixing the dyeing composition of this invention, at the time of use, with a sufficient amount of an oxidising agent, generally as a solution to develop the expected colour, and then in applying the resulting mixture to the hair.

The oxidising solution typically contains hydrogen peroxide, and preferably a hydrogen peroxide solution of 20 volumes strength, as the oxidising agent. The mixture thus obtained is applied to the hair and left for, say, 10 to 30 minutes, after which the hair is rinsed, optionally shampooed, and rinsed again and dried.

Of course, the process according to the invention can also be carried out in several stages, at least one of the stages being applying the composition according to the invention to the hair, the second stage consisting in applying a composition containing direct dyestuffs, such as those mentioned above.

The following Examples further illustrate the present invention.

EXAMPLE 1

The following dyeing composition is prepared:

| | | |
|---|---|---|
| Para-phenylenediamine (0.023 mol) | 2.5 | g |
| N—Ethyl-N—$\beta$-hydroxyethyl-para-phenylene-diamine dihydrochloride (0.046 mol) | 11.7 | g |
| Carbopol 934 | 1.5 | g |
| 96° strength ethanol | 11 | g |
| Butylglycol | 5 | g |
| Trimethylcetylammonium bromide | 1 | g |
| Trilon B | 0.1 | g |
| 22° B strength ammonia solution | 15 | g |
| Thioglycolic acid | 0.2 | g |
| Water q.s.p. | 100 | g |
| pH 9.2 | | |

100 g of hydrogen peroxide of 20 volumes strength are added at the time of use. When applied to 90% naturally white hair for 30 minutes at 30° C., this mixture imparts to the hair, after rinsing and shampooing a black colouration with a blue sheen.

After an application time on the head of 30 minutes, a sample of the dyeing composition is chromatographed on a Schleicher and Schüll F 1500 LS 254 plate.

A spot of a solution of ortho-aminophenol is applied in a first stage, at the point where the oxidising dyeing solution is to be applied in a second stage. It is found that the dyeing solution does not contain a detectable amount of Bandrowsky's base.

EXAMPLE 2

The following dyeing composition is prepared:

| | | |
|---|---|---|
| Para-phenylenediamine (0.023 mol) | 2.5 | g |
| N,N—Di-β-hydroxyethyl-para-phenylenediamine dihydrochloride (0.046 mol) | 12.46 | g |
| Sodium lauryl-sulfate containing 2 mols of ethylene oxide (per mol of sulphate) | 20 | g |
| Trilon B | 0.2 | g |
| 35° B strength sodium bisulphite solution | 1 | g |
| Hydroquinone | 0.15 | g |
| 22° B strength ammonia solution | 15 | g |
| Water q.s.p. pH 9.3 | 100 | g |

100 g of hydrogen peroxide of 20 volumes strength are added at the time of use. When applied to 90% naturally white hair for 30 minutes at 30° C., this mixture imparts to the hair, after rinsing and shampooing, a black colouration. Exactly as above, the formation of Bandrowsky's base is not observed by chromatography.

A dyeing mixture which differs from the above mixture only by the absence of N,N-di-β-hydroxyethyl-para-phenylenediamine dihydrochloride imparts to 90% naturally white hair, after rinsing and shampooing, an extremely dark colouration with a purple-red sheen.

EXAMPLE 3

The following dyeing composition is prepared:

| | | |
|---|---|---|
| Para-phenylenediamine (0.0185 mol) | 2 | g |
| N—Ethyl-N—β-hydroxyethyl-para-phenylenediamine dihydrochloride (0.037 mol) | 9.36 | g |
| 2-Amino-3-nitro-isopropylbenzene | 1.3 | g |
| Carbopol 934 | 1.5 | g |
| 96° strength ethanol | 11 | g |
| Butylglycol | 5 | g |
| Trimethylcetylammonium bromide | 1 | g |
| Trilon B | 0.1 | g |
| 22° B strength ammonia solution | 12 | g |
| Thioglycolic acid | 0.2 | g |
| Water q.s.p. pH 9.3 | 100 | g |

100 g of hydrogen peroxide of 20 volumes strength are added at the time of use. When applied to 90% naturally white hair for 30 minutes at 25° C., this mixture imparts to the hair, after rinsing and shampooing, a black colouration.

EXAMPLE 4

The following dyeing composition is prepared:

| | | |
|---|---|---|
| Para-phenylenediamine (0.0138 mol) | 1.5 | g |
| N,N—Di-β-hydroxyethyl-para-phenylenediamine dihydrochloride (0.0138 mol) | 3.74 | g |
| Oxyethyleneated oleyl alcohol containing 2 mols of ethylene oxide | 4.5 | g |
| Oxyethyleneated oleyl alcohol containing 4 mols of ethylene oxide | 4.5 | g |
| Ethomeen TO$_{12}$ | 4.5 | g |
| Diethanolamides of copra fatty acids | 9 | g |
| Propylene glycol | 4 | g |
| Butylglycol | 8 | g |
| 96° strength ethanol | 6 | g |
| Masquol DTPA | 2 | g |
| Thioglycolic acid | 0.5 | g |
| 22° B strength ammonia solution | 10 | g |
| Water q.s.p. pH 9.3 | 100 | g |

100 g of hydrogen peroxide of 20 volumes strength are added at the time of use. When applied to 90% naturally white hair for 30 minutes at 30°, this mixture imparts to the hair, after rinsing and shampooing, a raven black colouration.

Under the same conditions of application, a dyeing mixture which differs from the mixture described above only by the absence of N,N-di-β-hydroxyethyl-para-phenylenediamine dihydrochloride imparts to 90% naturally white hair, after rinsing and shampooing, a purple-red brown colouration.

EXAMPLE 5

The following dyeing composition is prepared:

| | | |
|---|---|---|
| Para-phenylenediamine (0.0139 mol) | 1.5 | g |
| N—Ethyl-N—β-hydroxyethyl-para-phenylenediamine dihydrochloride (0.0139 mol) | 3.5 | g |
| Oxyethyleneated oleyl alcohol containing 2 mols of ethylene oxide | 4.5 | g |
| Oxyethyleneated oleyl alcohol containing 4 mols of ethylene oxide | 4.5 | g |
| Ethomeen TO$_{12}$ | 4.5 | g |
| Diethanolamides of copra fatty acids | 9 | g |
| Propylene glycol | 4 | g |
| Butylglycol | 8 | g |
| 96° strength ethanol | 6 | g |
| Masquol DTPA | 2 | g |
| Thioglycolic acid | 0.5 | g |
| 22° B strength ammonia solution | 10 | g |
| Water q.s.p. pH 9.4 | 100 | g |

100 g of hydrogen peroxide of 20 volumes strength are added at the time of use. When applied to 90% naturally white hair for 30 minutes at 30°, this mixture imparts to the hair, after rinsing and shampooing, a black colouration with a purplish-blue sheen.

EXAMPLE 6

The following dyeing composition is prepared:

| | | |
|---|---|---|
| Para-phenylenediamine (0.0139 mol) | 1.5 | g |
| N—Ethyl-N—β-hydroxyethyl-para-phenylenediamine dihydrochloride (0.0278 mol) | 7 | g |
| 2-N—(β-Hydroxyethyl)-amino-5-nitroanisole | 2 | g |
| Carboxymethylcellulose | 2 | g |
| Ammonium lauryl-sulphate | 5 | g |
| Ammonium acetate | 1 | g |
| Propylene glycol | 8 | g |
| Masquol DTPA | 2 | g |
| Butylglycol | 8 | g |
| 22° B strength ammonia solution | 10 | g |
| Water q.s.p. pH 9.6 | 100 | g |

100 g of hydrogen peroxide of 20 volumes strength are added at the time of use. When applied for 25 minutes at 27° C. to hair which has been bleached straw yellow, this mixture imparts to the hair, after rinsing and shampooing, a black colouration with a blue sheen.

EXAMPLE 7

The following dyeing composition is prepared:

| | | |
|---|---|---|
| Para-phenylenediamine (0.0125 mol) | 1.35 | g |
| N—Ethyl-N—β-hydroxyethyl-para-phenylene- | | |
| diamine dihydrochloride (0.0166 mol) | 4.21 | g |
| 3-Nitro-4-N—(β-hydroxyethyl)-aminophenol | 1.8 | g |
| Carbopol 934 | 1.5 | g |
| 96° strength ethanol | 11 | g |
| Butylglycol | 5 | g |
| Trimethylcetylammonium bromide | 1 | g |
| Trilon B | 0.1 | g |
| 22° B strength ammonia solution | 10 | g |
| Thioglycolic acid | 0.2 | g |
| Water q.s.p. | 100 | g |
| pH 9.6 | | |

100 g of hydrogen peroxide of 20 volumes strength are added at the time of use. When applied for 30 minutes at 30° C. to hair which has been bleached white, this mixture imparts to the hair, after rinsing and shampooing, a very dark brown colouration with a slight purple sheen.

Under the same conditions of application, a dyeing mixture which differs from the above mixture only by the absence of N-ethyl-N-β-hydroxyethyl-para-phenylenediamine dihydrochloride imparts to hair which has been bleached white, after rinsing and shampooing, an intense, very red, copper colouration.

EXAMPLE 8

The following dyeing composition is prepared:

| | | |
|---|---|---|
| Para-phenylenediamine (0.011 mol) | 1.2 | g |
| N,N—Di-β-hydroxyethyl-para-phenylenediamine | | |
| dihydrochloride (0.017 mol) | 4.58 | g |
| 2-Methyl-4-amino-5-nitrophenol | 1.6 | g |
| Carbopol 934 | 1.5 | g |
| 96° strength ethanol | 11 | g |
| Butylglycol | 5 | g |
| Trimethylcetylammonium bromide | 1 | g |
| Trilon B | 0.1 | g |
| 22° B strength ammonia solution | 10 | g |
| Thioglycolic acid | 0.2 | g |
| Water q.s.p. | 100 | g |
| pH 9.7 | | |

100 g of hydrogen peroxide of 20 volumes strength are added at the time of use. When applied to 90% naturally white hair for 30 minutes at 28° C., this mixture imparts to the hair, after rinsing and shampooing, a black colouration with a violet sheen.

Under the same conditions of application, a dyeing mixture which differs from the mixture described above only by the absence of N,N-di-β-hydroxyethyl-para-phenylenediamine dihydrochloride imparts a mahogany colouration to 90% naturally white hair.

EXAMPLE 9

The following dyeing composition is prepared:

| | | |
|---|---|---|
| Para-phenylenediamine (0.01 mol) | 1.08 | g |
| N—Ethyl-N—β-hydroxyethyl-para-phenylene- | | |
| diamine dihydrochloride (0.01 mol) | 2.53 | g |
| 3-Nitro-4-aminophenol | 1.2 | g |
| Oxyethyleneated oleyl alcohol containing | | |
| 2 mols of ethylene oxide | 4.5 | g |
| Oxyethyleneated oleyl alcohol containing | | |
| 4 mols of ethylene oxide | 4.5 | g |
| Ethomeen TO₁₂ | 4.5 | g |
| Diethanolamides of copra fatty acids | 9 | g |
| Propylene glycol | 4 | g |
| Butylglycol | 8 | g |
| 96° strength ethanol | 6 | g |
| Masquol DTPA | 2 | g |
| Thioglycolic acid | 0.5 | g |
| 22° B strength ammonia solution | 10 | g |
| Water q.s.p. | 100 | g |
| pH 9.8 | | |

100 g of hydrogen peroxide of 20 volumes strength are added at the time of use.

When applied for 20 minutes at 26° C. to hair which has been bleached white, this mixture imparts to the hair, after rinsing and shampooing, a brown colouration with a coppery sheen.

A dyeing mixture which differs from the mixture described above only by the absence of N-ethyl-N-β-hydroxyethyl-para-phenylenediamine dihydrochloride imparts to hair which has been bleached white, after rinsing and shampooing, a flamboyant red colouration.

EXAMPLE 10

The following dyeing composition is prepared:

| | | |
|---|---|---|
| Para-phenylenediamine (0.0092 mol) | 1 | g |
| N—Ethyl-N—β-hydroxyethyl-para-phenylene- | | |
| diamine sulphate monohydrate (0.0185 mol) | 5.48 | g |
| Remcopal 334 | 21 | g |
| Remcopal 349 | 24 | g |
| Oleic acid | 4 | g |
| Butylglycol | 3 | g |
| 96° strength ethanol | 10 | g |
| Masquol DTPA | 2.5 | g |
| 35° B strength sodium bisulphite solution | 1 | g |
| 22° B strength ammonia solution | 10 | g |
| Water q.s.p. | 100 | g |
| pH 9 | | |

100 g of hydrogen peroxide of 20 volumes strength are added at the time of use. When applied to 90% naturally white hair for 20 minutes at 25° C., this mixture imparts to the hair, after rinsing and shampooing, a brown colouration.

A dyeing mixture which differs from the above mixture only by the absence of N-ethyl-N-β-hydroxyethyl-para-phenylenediamine sulphate monohydrate imparts a copper-red chestnut colouration to 90% naturally white hair.

EXAMPLE 11

The following dyeing composition is prepared:

| | | |
|---|---|---|
| Para-phenylenediamine (0.007 mol) | 0.756 | g |
| N,N—Di-β-hydroxyethyl-para-phenylene- | | |
| diamine dihydrochloride (0.01 mol) | 2.69 | g |
| 2-Amino-3-nitrophenol | 0.21 | g |
| Oxyethyleneated oleyl alcohol containing | | |
| 2 mols of ethylene oxide | 4.5 | g |
| Oxyethyleneated oleyl alcohol containing | | |
| 4 mols of ethylene oxide | 4.5 | g |
| Diethanolamides of copra fatty acids | 10 | g |
| 35° B strength sodium bisulphite solution | 1 | g |
| Masquol DTPA | 2 | g |
| Propylene glycol | 4.0 | g |
| Butylglycol | 8 | g |
| 96° strength ethanol | 8 | g |
| 22° B strength ammonia solution | 10 | g |
| Water q.s.p. | 100 | g |
| pH 10 | | |

100 g of hydrogen peroxide of 20 volumes strength are added at the time of use. When applied to 90% naturally white hair for 30 minutes at 30° C., this mixture imparts to the hair, after rinsing and shampooing, a very dark brown colouration shaded with red.

Under the same conditions of application, a dyeing mixture which differs from the above mixture only by the absence of N,N-di-β-hydroxyethyl-para-phenylenediamine dihydrochloride imparts a copper-red chestnut colouration to 90% naturally white hair.

EXAMPLE 12

The following dyeing composition is prepared;

| | | |
|---|---|---|
| Para-phenylenediamine (0.0046 mol) | 0.5 | g |
| N—Etyl-N—β-hydroxyethyl-para-phenylene-diamine dihydrochloride (0.0046 mol) | 1.17 | g |
| 2-Amino-3-nitrophenol | 0.1 | g |
| Carboxymethylcellulose | 2 | g |
| Ammonium lauryl-sulphate | 5 | g |
| Ammonium acetate | 1 | g |
| Propylene glycol | 8 | g |
| Masquol DTPA | 2 | g |
| Thioglycolic acid | 0.4 | g |
| Butylglycol | 8 | g |
| 22° B strength ammonia solution | 10 | g |
| Water q.s.p. | 100 | g |
| pH 10.2 | | |

100 g of hydrogen peroxide of 20 volumes strength are added at the time of use.

When applied for 30 minutes at 28° C. to hair which has been bleached straw blond, this mixture imparts to the hair, after rinsing and shampooing, a deep chestnut colouration with a coppery sheen.

Under the same conditions of application, a dyeing mixture which differs from the above mixture only by the absence of N-ethyl-N-β-hydroxyethyl-para-phenylenediamine dihydrochloride imparts a red chestnut colouration to hair which has been bleached straw blond.

EXAMPLE 13

The following dyeing composition is prepared:

| | | |
|---|---|---|
| Para-phenylenediamine (0.005 mol) | 0.54 | g |
| N,N—Di-β-hydroxyethyl-para-phenylene-diamine dihydrochloride (0.005 mol) | 1.345 | g |
| 1-Methylamino-2-nitro-4-N,N—di-(β-hydroxyethyl)-aminobenzene | 0.7 | g |
| 2-N—(β-Hydroxyethyl)-amino-5-nitrophenoxy-ethanol | 0.45 | g |
| Oxyethyleneated oleyl alcohol containing 2 mols of ethylene oxide | 4.5 | g |
| Oxyethyleneated oleyl alcohol containing 4 mols of ethylene oxide | 4.5 | g |
| Ethomeen TO$_{12}$ | 4.5 | g |
| Diethanolamides of copra fatty acids | 9 | g |
| Propylene glycol | 4 | g |
| Butylglycol | 8 | g |
| 96° strength ethanol | 6 | g |
| Masquol DTPA | 2 | g |
| Thioglycolic acid | 0.5 | g |
| 22° B strength ammonia solution | 10 | g |
| Water q.s.p. | 100 | g |
| pH 10.3 | | |

100 g of hydrogen peroxide of 20 volumes strength are added at the time of use. When applied for 30 minutes at 28° C. to hair which has been bleached white, this mixture imparts to the hair, after rinsing and shampooing, a medium chestnut colouration with a golden sheen.

Under the same conditions of application, a dyeing mixture which differs from the above mixture only by the absence of N,N-di-β-hydroxyethyl-para-phenylenediamine dihydrochloride imparts a coppery light chestnut colouration to hair which has been bleached white.

EXAMPLE 14

The following dyeing composition is prepared;

| | | |
|---|---|---|
| Para-phenylenediamine (0.003 mol) | 0.324 | g |
| N—Ethyl-N—β-hydroxyethyl-para-phenylene-diamine dihydrochloride (0.003 mol) | 0.759 | g |
| Oxyethyleneated oleyl alcohol containing 2 mols of ethylene oxide | 4.5 | g |
| Oxyethyleneated oleyl alcohol containing 4 mols of ethylene oxide | 4.5 | g |
| Ethomeen TO$_{12}$ | 4.5 | g |
| Diethanolamides of copra fatty acids | 9 | g |
| Propylene glycol | 4 | g |
| Butylglycol | 8 | g |
| 96° strength ethanol | 6 | g |
| Masquol DTPA | 2 | g |
| Thioglycolic acid | 0.5 | g |
| Triethanolamine | 10 | g |
| Water q.s.p. | 100 | g |
| pH 8.9 | | |

100 g of hydrogen peroxide of 20 volumes strength are added at the time of use. When applied for 25 minutes at 28° C. to hair which has been bleached white, this mixture imparts to the hair, after rinsing and shampooing, an ashen medium chestnut colouration.

A dyeing mixture which differs from the mixture described above only by the absence of N-ethyl-N-β-hydroxyethyl-para-phenylenediamine dihydrochloride imparts to hair which has been bleached white, after rinsing and shampooing, a copper-red blond colouration.

EXAMPLE 15

The following dyeing composition is prepared:

| | | |
|---|---|---|
| Para-phenylenediamine (0.002 mol) | 0.216 | g |
| N,N—Di-β-hydroxyethyl-para-phenylene-diamine dihydrochloride (0.002 mol) | 0.538 | g |
| Sodium lauryl-sulphate containing 2 mols of ethylene oxide | 20 | g |
| Trilon B | 0.2 | g |
| 35° B strength sodium bisulphite solution | 1 | g |
| 22° B strength ammonia solution | 10 | g |
| Water q.s.p. | 100 | g |
| pH 10.8 | | | are added at the time of use. When applied to bleached hair for 25 minutes at 26° C., this mixture imparts to the hair, after rinsing and shampooing, an ashen beige colouration. Exactly as in the preceding examples, no formation of Bandrowsky's base in the composition applied to the hair is observed from chromatography on a Schleicher and Schüll F 1500 LS 254 plate.

Under the same conditions of application a dyeing mixture which differs from the mixture described above only by the absence of N,N-di-β-hydroxyethyl-para-phenylenediamine dihydrochloride imparts a coppery light blond colouration to bleached hair.

In the preceding Examples, the commercial products are constituted as follows:

Remcopal 334: oxyethyleneated nonylphenol containing 4 mols of ethylene oxide, sold by Gerland, Remcopal 349: oxyethyleneated nonylphenol containing 9 mols of ethylene oxide, sold by Gerland, Ethomeen TO₁₂: oxyethyleneated oleylamine containing 12 mols of ethylene oxide, sold by Armour Hess Chemical Ltd.,
Carbopol 934: crosslinked polyacrylic acid sold by Goodrich Chemical,
Trilon B: ethylenediaminetetraacetic acid, and
Masquol DTPA: the pentasodium salt of diethylenetriaminepentaacetic acid, sold by Protex.

We claim:

1. A composition suitable for dyeing hair which contains, in a cosmetically acceptable medium, para-phenylenediamine or a cosmetically acceptable salt thereof and one or more compounds corresponding to the formula (I)

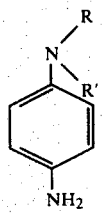

in which R denotes an alkyl or hydroxyalkyl group and R' denotes a hydroxyalkyl group, the alkyl groups having 2 to 4 carbon atoms, or a cosmetically acceptable salt thereof, in a molar ratio para-phenylenediamine/-compound(s) of the formula (I) which is about 0.5:1 in the case the composition contains para-phenylenediamine in an amount of 1.5 to 2.5% by weight and does not exceed 1:1 and is not less than 0.5:1 in the case para-phenylenediamine is present in an amount of 0.2 to 1.5% by weight.

2. A composition according to claim 1, in which the compound corresponding to the formula (I) is N,N-di-β-hydroxyethyl-para-phenylenediamine or N-ethyl-N-β-hydroxyethyl-para-phenylenediamine.

3. A composition according to claim 1 or 2, which contains 0.2 to 2.5% by weight of para-phenylenediamine.

4. A composition according to claim 1 which has a pH of 8 to 11.5.

5. A composition according to claim 1 in which the cosmetically acceptable medium is aqueous and contains one or more of the following: an anionic, cationic, non-ionic or amphoteric water-soluble surface-active agent or mixture thereof, an organic solvent, thickener, antioxidant, penetrating agent, sequestering agent, film-forming polymer, buffer or perfume.

6. A composition according to claim 1 which contains one or more direct dyestuffs.

7. A composition according to claim 6 in which the direct dyestuff is a nitrobenzene derivative.

8. Process for dyeing the hair, which comprises mixing a composition as defined in claim 1 with an oxidising agent, applying the resulting mixture to the hair for 10 to 30 minutes, rinsing the hair, optionally washing and rinsing it again, and drying it.

9. Process for dyeing the hair, which comprises applying thereto a composition as defined in claim 1 and after the hair has been impregnated, a dyeing composition containing a nitrobenzene direct dyestuff is applied.

* * * * *